United States Patent
Zirngibl

(10) Patent No.: US 10,772,514 B2
(45) Date of Patent: Sep. 15, 2020

(54) METHOD OF OPERATING A LONG-TERM BLOOD PRESSURE MEASUREMENT DEVICE

(71) Applicant: MULLER & SEBASTIANI ELEKTRONIK GMBH, Ottobrunn (DE)

(72) Inventor: Christian Zirngibl, Zorneding (DE)

(73) Assignee: MULLER & SEBASTIAN ELEKTRONIK GMBH, Ottobrun (DE)

( * ) Notice: Subject to any disclaimer, the term of this patent is extended or adjusted under 35 U.S.C. 154(b) by 254 days.

(21) Appl. No.: 15/473,410

(22) Filed: Mar. 29, 2017

(65) Prior Publication Data

US 2017/0332921 A1 Nov. 23, 2017

(30) Foreign Application Priority Data

Mar. 29, 2016 (DE) .......................... 10 2016 105 684

(51) Int. Cl.
*A61B 5/021* (2006.01)
*A61B 5/00* (2006.01)
*A61B 5/022* (2006.01)
*A61B 5/0225* (2006.01)
*A61B 5/11* (2006.01)
(Continued)

(52) U.S. Cl.
CPC .......... *A61B 5/02141* (2013.01); *A61B 5/022* (2013.01); *A61B 5/02125* (2013.01); *A61B 5/02233* (2013.01); *A61B 5/02255* (2013.01); *A61B 5/11* (2013.01); *A61B 5/6815* (2013.01); *A61B 5/6823* (2013.01); *A61B 5/6824* (2013.01); *A61B 5/6826* (2013.01); *A61B 5/0432* (2013.01); *A61B 5/04085* (2013.01); (Continued)

(58) Field of Classification Search
None
See application file for complete search history.

(56) References Cited

U.S. PATENT DOCUMENTS 7,374,542 B2   5/2008   Kuchler
9,072,433 B2 * 7/2015   Chen ................... A61B 5/02108
(Continued)

FOREIGN PATENT DOCUMENTS

DE   102007050598 A1   4/2009
DE   102005014048 B4   8/2010

OTHER PUBLICATIONS

German Patent Search Report dated Feb. 27, 2017; received in German Patent Appl. No. 10 2016 105 684 7; 8 pages.

*Primary Examiner* — Sean P Dougherty
*Assistant Examiner* — Benjamin S Melhus
(74) *Attorney, Agent, or Firm* — Kilpatrick Townsend & Stockton LLP

(57) ABSTRACT

The invention relates to a method of operating a long-term blood pressure measurement device having a measurement sensor for detecting a pulse wave signal, having a measurement sensor for body current signals, having a pressure cuff for a non-invasive determination of the blood pressure, having a control and evaluation unit for determining blood pressure values, on the one hand from signals acquired by means of the pressure cuff (pressure cuff signals), and, on the other hand from a pulse wave transit time that is derived from body current signals and pulse wave signals, and having a memory for storing blood pressure values.

12 Claims, 1 Drawing Sheet

(51) Int. Cl.
 *A61B 5/0432* (2006.01)
 *A61B 5/0408* (2006.01)
(52) U.S. Cl.
 CPC ..... *A61B 5/6817* (2013.01); *A61B 2560/0223* (2013.01)

(56) References Cited

U.S. PATENT DOCUMENTS

2009/0050544 A1\* 2/2009 Zhang ................... A61B 5/021
 210/90
2010/0160798 A1 6/2010 Banet et al.
2018/0199824 A1\* 7/2018 Centen ................. A61B 5/0295

\* cited by examiner

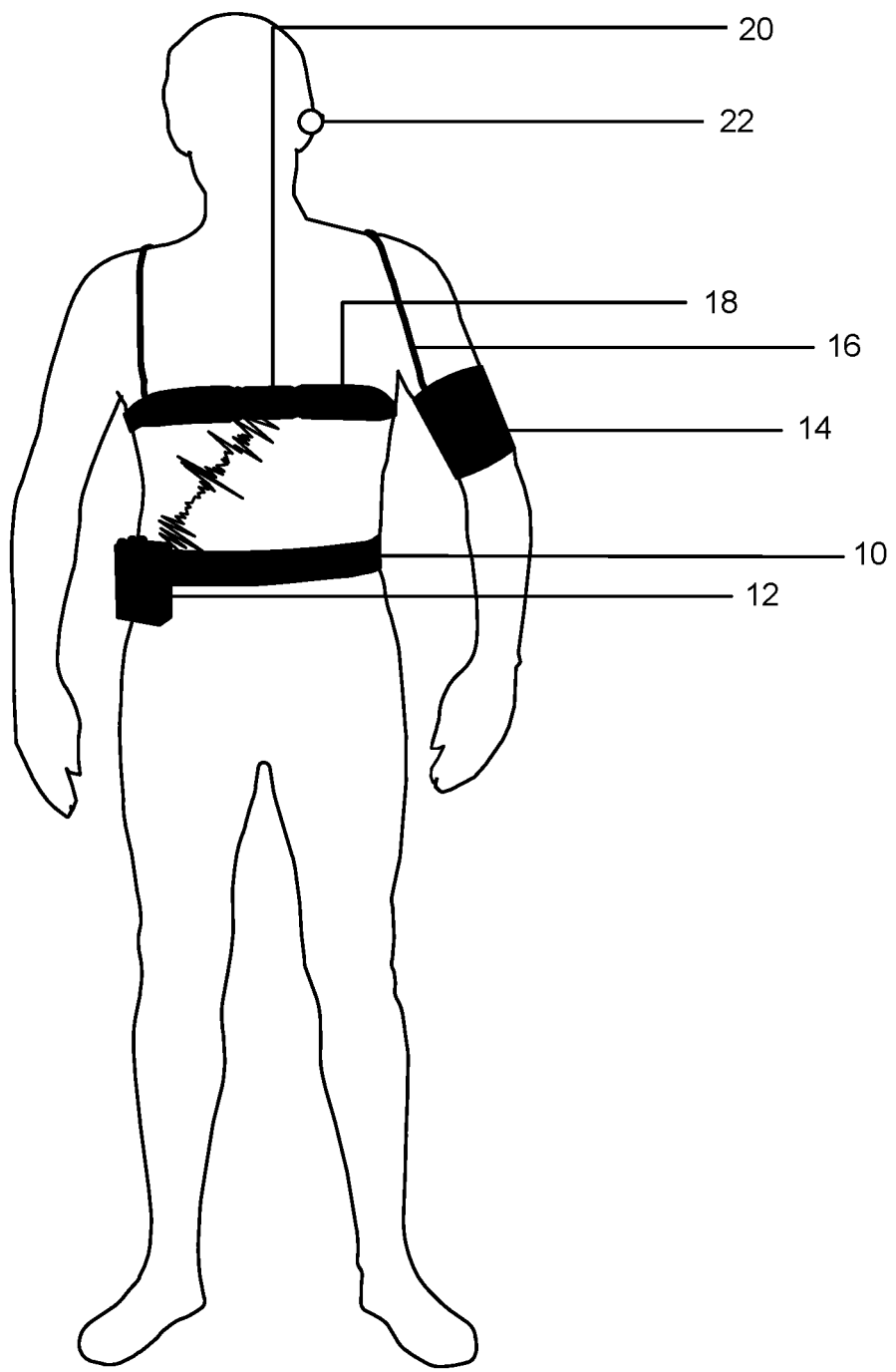

METHOD OF OPERATING A LONG-TERM BLOOD PRESSURE MEASUREMENT DEVICE

CROSS-REFERENCES TO RELATED APPLICATIONS

This application claims priority to German Patent Application No. 102016105684.7, filed Mar. 29, 2016, which is incorporated by reference herein.

BACKGROUND OF THE INVENTION

The present invention relates to a method of operating a long-term blood pressure measurement device having a measurement sensor for detecting a pulse wave signal, having a measurement sensor for body current signals, having a pressure cuff for a non-invasive determination of the blood pressure, having a control and evaluation unit for determining blood pressure values, on the one hand from signals acquired by means of the pressure cuff (pressure cuff signals), and, on the other hand from a pulse wave transit time that is derived from body current signals and pulse wave signals, and having a memory for storing blood pressure values.

Such devices have been known for some time and are used e.g. in mobile form to be worn on the body of persons over comparatively long time periods of several hours or several days. In known devices, blood pressure measurements as a rule take place periodically at fixedly predefined time intervals, e.g. every 15 or 30 minutes. This has the result in a disadvantageous manner that significant blood pressure changes remain unrecognized when they occur in the time intervals between two measurements. Furthermore, with regularly occurring measurements, unnecessary measurements are also carried out with unchanged blood pressure values, with these measurements then putting unnecessary stress on or unnecessarily irritating the persons wearing the device.

With known devices of the named kind that are equipped with a measurement sensor for detecting a pulse wave signal, a blood pressure measurement can advantageously be triggered via the pressure cuff not only at regular time intervals, but also in dependence on the progression of the pulse wave signal. A blood pressure measurement can therefore always be triggered via the pressure cuff, for example, when there is an indication of a noticeable blood pressure value due to the progression of the pulse wave signal. Such a long-term blood pressure measurement device is described, for example, in the German patent application DE 10 2007 050 598.3. For example, the fact that the pulse wave signal is detected via a measurement sensor that has to be fixed to the finger or to the earlobe of a person, which is often irritating for the person, in particular in daily life, and which also frequently results in artifacts in the pulse wave signal due to movements of the person, is a disadvantage of this long-term blood pressure measurement device.

It is furthermore a disadvantage in the mentioned long-term blood pressure measurement device that the actual measurement of the blood pressure takes place via the pressure cuff, which for persons is associated with a high pressure on the upper arm, on the one hand, and with a comparatively loud noise of the compressed air source acting on the pressure cuff, on the other hand. This has an irritating effect in everyday life and can also have the result that blood pressure values are falsified since some people are agitated by the blood pressure measurement they can clearly perceive, which then results in increased values and ultimately in values unrealistic for a normal everyday situation.

It is furthermore known to use devices of the initially named kind such that blood pressure values are determined in long-term operation only from the pulse wave transit time by means of different calculation methods, with a blood pressure measurement by means of the pressure cuff only being used for an initial calibration or for a later recalibration. The calculation and calibration methods used here, however, disadvantageously frequently result in falsified blood pressure values.

BRIEF SUMMARY OF THE INVENTION

It is an object of the invention to further develop the known long-term blood pressure measurement devices such that persons are disturbed as little as possible by the carrying out of the blood pressure measurements in long-term operation and such that simultaneously a high accuracy can be achieved in the determined blood pressure values.

DETAILED DESCRIPTION OF THE INVENTION

In accordance with the invention, this object is satisfied by the features of claim 1 and in particular in that, for calibration with an initially named long-term blood pressure measurement device, first a) a blood pressure value is determined from pressure cuff signals and in parallel therewith a pulse wave transit time is determined;

b) a correlation between the blood pressure value and the pulse wave transit time corresponding thereto takes place in the form of a value pair in the memory; and c) in that the steps a) and b) are repeated for different blood pressure values at time intervals, whereby a correlation table is produced in the memory with a plurality of value pairs of a respective blood pressure value and a pulse wave transit time; and in that then, in long-term operation, d) pulse wave transit times are determined at consecutive points in time whose corresponding blood pressure values are each determined by means of the correlation table or by means of an approximation function acquired therefrom and are stored together with the associated points in time.

In accordance with the invention, different blood pressure values are therefore first determined by means of pressure cuff signals as part of a calibration, with the pulse wave transit time then current at the respective point in time also being determined simultaneously with the determination of the respective blood pressure values. A plurality of value pairs of blood pressure and pulse wave transit time can thus be formed, whereby ultimately the correlation table in accordance with the invention is produced. When only the pulse wave transit time is then determined without the use of the pressure cuff in the subsequent long-term operation, the associated blood pressure value can be taken from the correlation table provided that the pulse wave transit time determined in long-term operation is included in the correlation table. An extrapolation of the determined value pairs can be carried out, for example as part of the calibration, for the pulse wave transit times not included in the correlation table such that ultimately all the possible pulse wave transit times with the associated blood pressure values are included in the correlation table. It is alternatively possible to determine an approximation function via the determined value pairs as part of the calibration that comprises the value pairs in the best possible manner such that then ultimately all the blood pressure values can be determined via this approximation function from the pulse wave transit times determined in long-term operation.

The respective blood pressure value that occurs can be determined very accurately and in an non-falsified manner from the pulse wave transit times in long-term operation by these methods in accordance with the invention. The blood pressure values determined in accordance with the invention in this respect correspond to the systolic blood pressure.

A further substantial advantage of the device in accordance with the invention comprises the blood pressure generally being measured during long-term operation without a pressure cuff only by a suitable evaluation of the body current signals and pulse wave signals. In this respect, the pulse wave transit time that ultimately indicates how long it takes until a pulse wave triggered by a heartbeat reaches the location of the measurement sensor for the pulse wave signal is determined from the time relationship between the body current signals, preferably recorded close to the heart, and the pulse wave signals. The start of the pulse wave transit time interval results from the body current signal and the end of this time interval results from the pulse wave signal. The blood pressure can then be determined after the previous calibration in accordance with the invention in the already explained manner from the pulse wave transit time. It is thus possible without problem not only to carry out a blood pressure measurement in accordance with the invention in long-term operation every 15 or 30 minutes, but considerably more frequently, if not even continuously, without the wearing of the long-term blood measurement device thereby becoming less pleasant for the person. A monitoring of the blood pressure of the person that has a lot fewer gaps thus becomes possible without any additional strain caused by an activation of the pressure cuff.

The blood pressure measurement in long-term operation is thus comparatively pleasant for the person since the person anyway always wears the measurement sensor for body current signals and pulse wave signals at the body, with the person not being able to perceive either in a tactile or acoustic manner whether these measurement sensors are active or not. This means that the person ultimately does not notice at all when a blood pressure measurement is taking place via body current signals and pulse wave signals such that the person is not impaired in any way in his everyday life here and also no measurement values can be falsified due to the imperceptible measurement.

The long-term blood pressure measurement in accordance with the invention thus provides the possibility of carrying out blood pressure measurements in a manner pleasant for the person without using the pressure cuff and of only carrying out the blood pressure measurement via the pressure cuff for calibration purposes or only from time to time in order, for example, to verify the blood pressure values determined without a pressure cuff.

The calibration in accordance with the invention takes place by a plurality of measurements at different points in time. At these points in time, the pressure cuff can be respectively applied again; it is alternatively also possible to leave the pressure cuff applied permanently over a time period of several hours.

The calibration preferably takes place over a time period of 24 hours, with the individual measurements being distributed over this time period.

The individual measurements during the calibration can be triggered in an automated manner, for example, and can take place at regular time intervals. Alternatively or additionally, measurements can also be triggered individually by the patient during the calibration, in particular whenever the patient suspects a change of his blood pressure values. Such changers can, for example, be triggered by agitation, physical activity or by a change in the measurement conditions (walking, standing, sitting, lying).

It is additionally or alternatively possible that the pulse wave transit time is determined continuously during the calibration and that a blood pressure measurement by means of pressure cuff signals is triggered when a change of the pulse wave transit time disposed above a predefined threshold is detected. A blood pressure measurement can be triggered in an automated manner in this manner whenever a change of the blood pressure value is very likely present.

It has already been explained that the blood pressure values are determined from the correlation table in accordance with the invention or via the approximation function determined in accordance with the invention in long-term operation. It is preferred in this respect if an individual correlation table or approximation function is determined for every patient to be examined as part of the calibration.

It is particularly preferred if a respective individual calibration takes place under different measurement conditions (walking, standing, sitting, lying) such that a respective separate correlation table or approximation function is present for the different measurement conditions. The correlation table or approximation function used in long-term operation is then always selected or changed in dependence on the measurement conditions respectively present in long-term operation.

If different correlation tables or approximation functions should be used for different measurement conditions, it is particularly advantageous if the measurement condition respectively present is determined continuously during the calibration and a blood pressure measurement by means of pressure cuff signals is at least triggered when a change of the measurement condition is detected.

In order then to be able to activate the correlation table or approximation function belonging to the respectively valid measurement condition in long-term operation, it is sensible if the measurement condition respectively present is determined with reference to motion sensors and/or positional sensors during long-term operation. These sensors are then preferably elements of the measurement device used in accordance with the invention.

It is particularly advantageous if the measurement sensor for detecting the pulse wave signal is adapted for fastening in or at the ear, at the finger or at the wrist of a person. A fastening in the ear is particularly preferred in this respect since the measurement sensor is in this case located in the auditory canal of the person like an ITE hearing aid and not, for instance, at the earlobe or behind the ear as with BTE hearing aids. This is not only of substantial advantage with respect to the comfort in wear, but also under esthetic aspects since the measurement sensor can only be perceived by third parties when looking intensely. In addition, much fewer artifacts that falsify the pulse wave signal occur with the measurement sensor in accordance with the invention than with measurement sensors that are attached to the finger or to the earlobe. In addition, it is of advantage here in the determination of the pulse wave transit time that the distance between the heart and the ear is comparatively short such that only very small errors can occur in the pulse wave transit time determination here.

Individual or all the measurement sensors can be coupled to the control and evaluation unit via a wireless connection. The ANT+ standard or Bluetooth are suitable for such a coupling.

The measurement sensor for body current signals can comprise at least two electrodes, but preferably also three or more electrodes, and can be fastened to a chest strap that is comfortable to wear. A transmitter can then likewise be located at the chest strap and transmits the recorded body current signals to the control and evaluation unit.

In a corresponding manner, the measurement sensor can have a transmitter for the pulse wave signal in its housing and the pulse wave signals can be transmitted via said transmitter to the control and evaluation unit.

The control and evaluation unit is preferably accommodated in a housing that can be fastened to the wrist of a person or to a strap respectively a belt. This allows a particularly comfortable wearing of the long-term blood pressure measurement device. On the accommodation of the control and evaluation unit in a housing at the wrist of a person, it is of advantage that measured values delivered from the measurement sensors or signals derived therefrom can be read out without problem by the person at a display of the housing.

If the control and evaluation unit is accommodated in a housing that can be fastened to the strap, the compressed air source for the pressure cuff can additionally also be accommodated in this housing. In this case, only a single housing is required for the compressed air source and the control and evaluation unit. On an arrangement of the control and evaluation unit at the wrist, in contrast, a housing has to be provided at the wrist and a housing for the compressed air source has to be provided at the strap of the person.

The long-term blood pressure measurement device in accordance with the invention can alternatively or additionally also be used as a mobile long-term ECG device, with it being preferred in this case if the device has one or more of the features that are disclosed in the German patent application DE 10 2007 050 601.7.

The long-term blood pressure measurement device in accordance with the invention can furthermore also have one or more of the features that are disclosed in the German patent application DE 10 2007 050 598.3.

Further preferred embodiments of the invention are explained in the dependent claims, in the description of the Figures and in the drawing.

The components of a possible embodiment of the long-term blood pressure measurement device in accordance with the invention will be explained in the following with reference to the only drawing:

BRIEF DESCRIPTION OF THE DRAWING

The person shown in the FIGURE wears a strap 10 to which a housing 12 is fastened. A control and evaluation unit, a compressed air source for a pressure cuff 14 and a signal memory at least for the storage of pulse wave transit times and blood pressure values are accommodated in this housing 12. The pressure cuff 14 that the person wears at the upper arm is connected to the compressed air source arranged in the housing 12 and to the control and evaluation unit likewise arranged there via a compressed air and signal line 16.

A reception unit is furthermore provided in the housing 12 that is suitable to receive body current signals and pulse wave signals.

The person shown furthermore wears a chest strap 18 at whose inner side two or three electrodes are arranged that are electrically coupled to a transmission unit 20 likewise fastened to the chest. The transmission unit 20 transmits the body current signals recorded by the electrodes in the chest strap 18 to the reception unit accommodated in the housing 12.

A measurement sensor 22 for pulse wave signals is located in the ear of the person shown. The housing of this measurement sensor 22 furthermore comprises a transmission unit that is suitable to transmit recorded pulse wave signals to the reception unit accommodated in the housing 12. values.

The invention claimed is:

1. A method of operating a long-term blood pressure measurement device, the long-term blood pressure measurement device comprising:
   a measurement sensor for detecting pulse wave signals;
   a measurement sensor for detecting body current signals;
   a pressure cuff for a non-invasive determination of the blood pressure;
   a control and evaluation unit for determining blood pressure values from pressure cuff signals acquired by means of the pressure cuff and from a pulse wave transit time that is derived from the body current signals and the pulse wave signals; and
   a memory for storing blood pressure values,
   the method comprising:
   calibrating said long-term blood pressure measurement device specifically for a patient by:
     a) determining a blood pressure value of the patient from pressure cuff signals from the pressure cuff and determining a pulse wave transit time of the patient, with the body current signals and the pulse wave signals, in parallel with the determination of said blood pressure value from the pressure cuff signals;
     b) correlating in the memory between said blood pressure value and said pulse wave transit time corresponding thereto in the form of a value pair; and
     c) repeating steps a) and b) for different blood pressure values at intervals in time over a first period comprising a plurality of hours, to produce a correlation table specific to the patient in the memory with a plurality of the value pairs, wherein each of the value pairs comprises a blood pressure value and a pulse wave transit time;
   detaching the pressure cuff from the long-term pressure measurement device after the calibrating of the long-term blood pressure measurement device; and
   operating said long-term blood pressure measurement device, after producing the correlation table, for a second period comprising a plurality of days with the pressure cuff detached from the long-term blood pressure measurement device, wherein operating said long-term blood pressure measurement device comprises:
   determining pulse wave transit times, with the body current signals and the pulse wave signals; and
   based on the pulse wave transit times determined while operating the long-term blood pressure measurement device determining blood pressure values using the correlation table over the second period.

2. The method in accordance with claim 1, wherein step c) of calibrating comprises at different points in time during the first period reapplying the pressure cuff.

3. The method in accordance with claim 1,
wherein step c) of calibrating comprises continually applying the pressure cuff over a plurality of different points in time during the first period.

4. The method in accordance with claim 1,
wherein measurements during the calibrating of the long-term pressure measurement device are take place at regular intervals in time during the first period.

5. The method in accordance with claim 1,
wherein measurements during the calibrating of the long-term pressure measurement device are triggered by the patient.

6. The method in accordance with claim 1,
the method comprising the further steps of determining the pulse wave transit time continuously during the calibrating of the long-term pressure measurement device; and
triggering a blood pressure measurement by means of pressure cuff signals when a change of the pulse wave transit time disposed above a predefined threshold is detected.

7. The method in accordance with claim 1,
wherein calibrating further comprising the step of:
calculating additional value pairs for pulse wave transit times not determined in steps a), b) and c); and including the additional value pairs in the correlation table used during operating the long-term blood pressure measurement device.

8. The method in accordance with claim 1,
wherein a respective individual calibration takes place under different measurement conditions such that a respective separate correlation table is present for the different measurement conditions.

9. The method in accordance with claim 8,
further comprising the steps of:
determining the measurement condition respectively present during the calibration and triggering a blood pressure measurement by means of pressure cuff signals when a change in the measurement condition is detected.

10. The method in accordance with claim 8,
wherein operating the long-term pressure measurement device further comprises the step of:
determining the measurement condition with reference to motion sensors and/or to positional sensors.

11. The method in accordance with claim 1,
wherein the measurement sensor for detecting the pulse wave signal is adapted for fastening in or at the ear, at the finger or at the wrist of a person.

12. The method in accordance with claim 1,
wherein a chest strap comprising at least two electrodes is used as the measurement sensor for body current signals.

* * * * *